US009108787B2

(12) United States Patent
Schneider

(10) Patent No.: US 9,108,787 B2
(45) Date of Patent: Aug. 18, 2015

(54) PROCESS FOR MANUFACTURING ABSORBENT PRODUCTS HAVING CUSTOMIZED GRAPHICS

(71) Applicant: The Procter & Gamble Company, Cincinnati, OH (US)

(72) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/329,138

(22) Filed: Jul. 11, 2014

(65) Prior Publication Data

US 2014/0318996 A1 Oct. 30, 2014

Related U.S. Application Data

(63) Continuation of application No. 12/476,288, filed on Jun. 2, 2009, now Pat. No. 8,776,683.

(51) Int. Cl.
*A61F 13/49* (2006.01)
*B65D 85/18* (2006.01)
(Continued)

(52) U.S. Cl.
CPC .......... *B65D 85/18* (2013.01); *A61F 13/15804* (2013.01); *A61F 13/51496* (2013.01); *B41F 17/003* (2013.01); *B65D 79/00* (2013.01); *A61F 2013/15243* (2013.01)

(58) Field of Classification Search
CPC .......... B65H 2801/57; B65H 2801/81; B65H 2801/84; A61F 13/15804; A61F 13/51496; A61F 2013/15243; B65D 85/18; B65D 79/00; B41F 17/003
USPC ......................................... 101/485; 270/21.1
See application file for complete search history.

(56) References Cited

U.S. PATENT DOCUMENTS 3,998,446 A 12/1976 Dent
4,393,386 A 7/1983 Di Giulio
(Continued)

FOREIGN PATENT DOCUMENTS

CH 609277 2/1979
DE 199208582 U1 11/1992
(Continued)

OTHER PUBLICATIONS

International Search Report, dated Aug. 11, 2010, 6 pages.

*Primary Examiner* — David Banh
(74) *Attorney, Agent, or Firm* — Charles R. Matson

(57) ABSTRACT

The present disclosure involves absorbent articles having customized graphics disposed inside packages labeled as containing customized articles. During the manufacturing process, customized absorbent articles are constructed with article identity graphics, and the packages to contain the customized articles are labeled with package identity graphics. A controller uses article and package identity graphics to track the manufacture of the customized articles and synchronize placement of the customized articles in the appropriately labeled packages. The methods disclosed herein provides for the manufacture of customized absorbent articles in series with the manufacture of absorbent articles having non-custom graphics. The substrates and/or components having the custom graphics in the manufacturing process are detected by a sensor that provides a feedback signal to a controller. The controller, in turn, commands a packing system to place the customized absorbent articles in packages; label the packages with a package identity graphic; and thereby create customized absorbent products.

11 Claims, 8 Drawing Sheets

(51) Int. Cl.
  *A61F 13/15* (2006.01)
  *A61F 13/514* (2006.01)
  *B41F 17/00* (2006.01)
  *B65D 79/00* (2006.01)

(56) References Cited

U.S. PATENT DOCUMENTS

| | | |
|---|---|---|
| 4,444,103 A | 4/1984 | Cronin |
| 4,535,694 A | 8/1985 | Fukuda |
| 4,695,278 A | 9/1987 | Lawson |
| 4,735,663 A | 4/1988 | Hasegawa |
| 4,753,649 A | 6/1988 | Pazdernik |
| 4,795,454 A | 1/1989 | Dragoo |
| 4,884,504 A | 12/1989 | Sillars |
| 4,893,559 A | 1/1990 | Sillars |
| 4,896,600 A | 1/1990 | Rogge et al. |
| 5,009,157 A | 4/1991 | Rogge et al. |
| 5,125,339 A | 6/1992 | Rogge |
| 5,127,746 A | 7/1992 | Rogge |
| 5,174,207 A | 12/1992 | Wallmann et al. |
| 5,184,551 A | 2/1993 | Wallmann et al. |
| 5,235,515 A | 8/1993 | Ungpiyakul et al. |
| 5,286,543 A | 2/1994 | Ungpiyakul et al. |
| 5,299,479 A | 4/1994 | Wallmann et al. |
| 5,373,788 A | 12/1994 | Schoen |
| 5,458,590 A | 10/1995 | Schleinz et al. |
| 5,503,076 A | 4/1996 | Yeo |
| 5,607,145 A | 3/1997 | Lovell |
| 5,695,855 A | 12/1997 | Yeo et al. |
| 5,735,210 A | 4/1998 | Rogge et al. |
| 5,897,541 A | 4/1999 | Uitenbroek et al. |
| 5,927,199 A | 7/1999 | Achelpohl et al. |
| 5,967,665 A | 10/1999 | MacDonald |
| 6,035,781 A | 3/2000 | Rogge et al. |
| 6,037,959 A | 3/2000 | Fassler et al. |
| 6,352,528 B1 | 3/2002 | Weber et al. |
| 6,454,095 B1 | 9/2002 | Brisebois et al. |
| 6,558,499 B1 | 5/2003 | Pargass et al. |
| 6,572,575 B1 | 6/2003 | Shimada et al. |
| 6,719,742 B1 | 4/2004 | McCormack et al. |
| 6,957,884 B2 | 10/2005 | Sharma et al. |
| 7,014,637 B1 | 3/2006 | Denti et al. |
| 7,172,667 B2 | 2/2007 | Vergona |
| 7,178,571 B2 | 2/2007 | Vergona |
| 7,340,417 B2 | 3/2008 | Kaufman et al. |
| 2002/0096628 A1 | 7/2002 | Yang |
| 2002/0097259 A1 | 7/2002 | Marshall et al. |
| 2002/0148749 A1 | 10/2002 | Briseboi et al. |
| 2002/0152001 A1 | 10/2002 | Knipp et al. |
| 2003/0126028 A1 | 7/2003 | Kaufman et al. |
| 2005/0061172 A1 | 3/2005 | Palmatier |
| 2005/0092427 A1 | 5/2005 | Verona |
| 2005/0116976 A1 | 6/2005 | Salacz et al. |
| 2005/0123661 A1 | 6/2005 | Kaufman et al. |
| 2005/0149389 A1 | 7/2005 | Odorzynski |
| 2005/0186416 A1 | 8/2005 | Sebastian et al. |
| 2005/0217791 A1 | 10/2005 | Costello et al. |
| 2006/0004333 A1 | 1/2006 | Olson |
| 2006/0020249 A1 | 1/2006 | Allen |
| 2006/0129115 A1 | 6/2006 | Visscher et al. |
| 2006/0135927 A1 | 6/2006 | Zander et al. |
| 2006/0167430 A1 | 7/2006 | Denti et al. |
| 2006/0247594 A1 | 11/2006 | Nickel et al. |
| 2007/0144937 A1 | 6/2007 | Gilroy |
| 2007/0239126 A1 | 10/2007 | Wilson et al. |
| 2008/0059324 A1 | 3/2008 | Bakken et al. |
| 2008/0077415 A1 | 3/2008 | Shannon et al. |
| 2008/0097875 A1 | 4/2008 | Kaufman et al. |
| 2008/0202954 A1 | 8/2008 | Knoblock et al. |

FOREIGN PATENT DOCUMENTS

| | | |
|---|---|---|
| DE | 199208583 U1 | 12/1992 |
| DE | 199211483 U1 | 1/1993 |
| DE | 10311514 B4 | 10/2004 |
| EP | 0 018 147 A1 | 10/1980 |
| EP | 0 029 312 A1 | 5/1981 |
| EP | 1 366 734 A1 | 12/2003 |
| EP | 1 704 842 A1 | 9/2006 |
| EP | 1 884 360 A2 | 2/2008 |
| JP | 58-71173 | 4/1983 |
| JP | 53-17357 | 3/1993 |
| JP | 10244656 | 9/1998 |
| JP | 11129595 | 5/1999 |
| JP | 11129596 | 5/1999 |
| JP | 2000000266 | 1/2000 |
| JP | 2004000648 | 1/2001 |
| JP | 2002191637 | 7/2002 |
| JP | 2002248128 | 9/2002 |
| JP | 2002369841 | 12/2002 |
| JP | 2003300655 | 10/2003 |
| JP | 2004160929 | 6/2004 |
| JP | 2005205798 | 8/2005 |
| JP | 2005273108 | 10/2005 |
| JP | 2005297461 | 10/2005 |
| NL | 7810516 | 4/1980 |
| WO | WO 91/08110 A1 | 6/1991 |
| WO | WO 99/32164 A1 | 7/1999 |
| WO | WO 99/47752 A1 | 9/1999 |
| WO | WO 99/60973 A1 | 12/1999 |
| WO | WO 00/13632 A1 | 3/2000 |
| WO | WO 00/76442 A1 | 12/2000 |
| WO | WO 01/21126 A1 | 3/2001 |
| WO | WO 02/096331 A2 | 12/2002 |
| WO | WO 2004/064872 A2 | 8/2004 |
| WO | WO 2005/102237 A1 | 11/2005 |

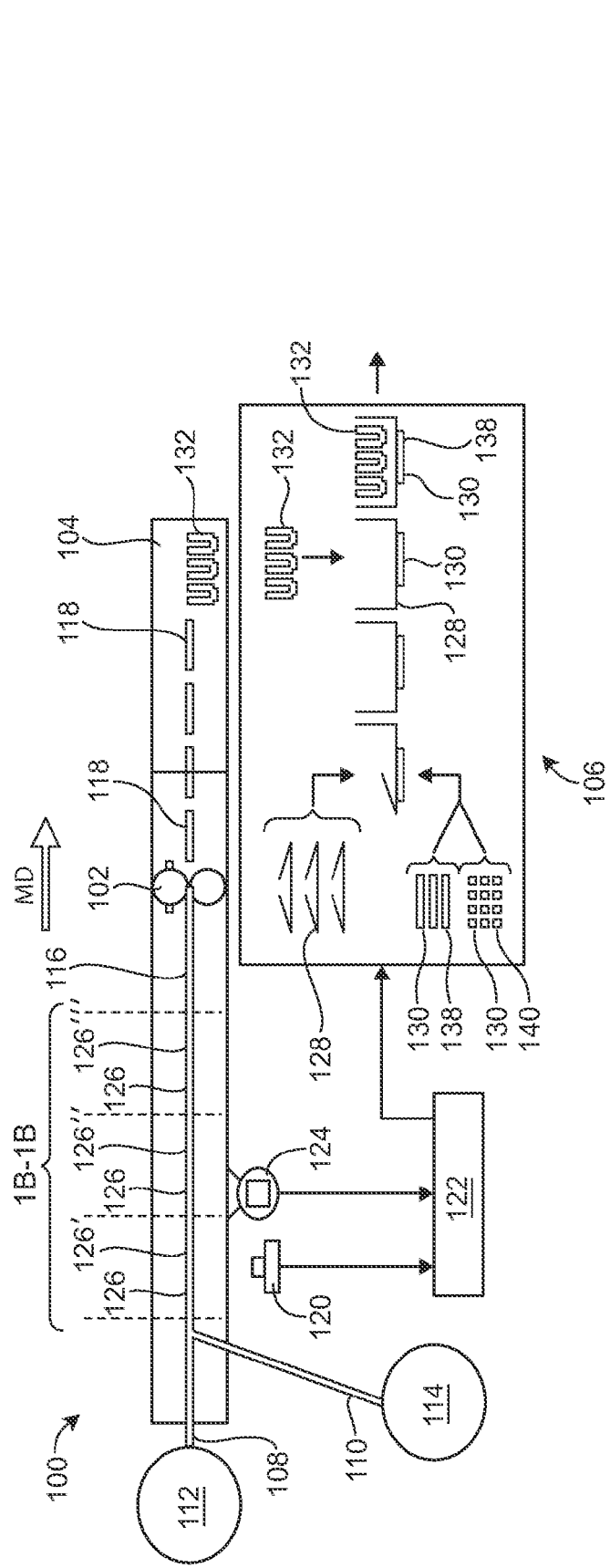
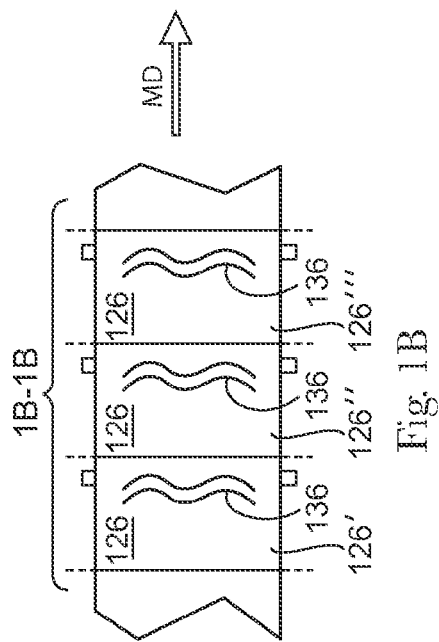
Fig. 1A
Fig. 1B

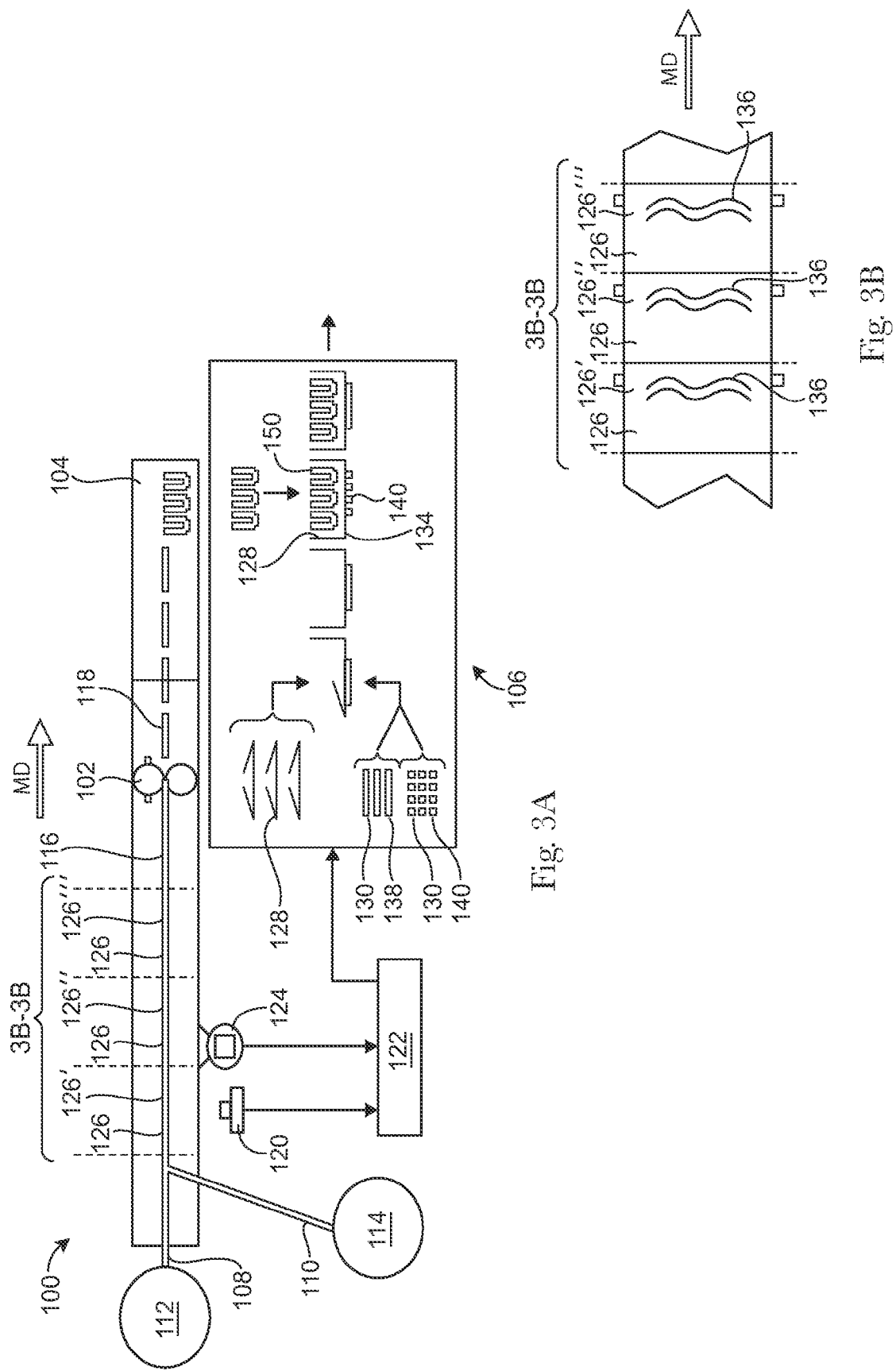

PROCESS FOR MANUFACTURING ABSORBENT PRODUCTS HAVING CUSTOMIZED GRAPHICS

CROSS REFERENCE TO RELATED APPLICATION

This application is a continuation of U.S. patent application Ser. No. 12/476,288, filed Jun. 2, 2009, which is hereby incorporated by reference.

FIELD OF THE INVENTION

The present disclosure relates to methods for producing absorbent products, and more particularly, methods for producing absorbent products having customized graphics.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. In some processes, graphics are printed on individual components and/or continuous webs of material used to assemble the absorbent articles.

Some consumers may prefer purchasing absorbent articles, such as diapers, having a number of different graphic designs printed thereon and provided in a single package. Further, some consumers may prefer purchasing diapers having customized graphics printed thereon. Various methods and apparatuses can be used to print different graphics on an advancing web of material used in the manufacture of absorbent articles. However, such methods and apparatuses may provide for limited numbers of different printed graphics, graphics with relatively low quality print, and/or require relatively low print and/or manufacture speeds. In addition, such methods and apparatuses may also require relatively expensive processes and equipment and may not be very flexible in allowing a user to change the type of graphics to be printed.

Thus, ink jet or some other type of non-contact printing may be used to print customized graphics, because of the relatively high degree of flexibility provided to easily change the graphics that are being printed. Because of the relatively slow speed associated with such non-contact printing techniques, custom graphics may be printed "off-line" on substrates prior to assembly of absorbent articles. The substrates having the custom graphics may then be utilized in a relatively high speed converting process to assemble customized absorbent products. In some instances, it may be desirable to manufacture customized articles in series with non-customized absorbent articles, which may present various challenges. For example, it may be difficult to efficiently and effectively segregate customized articles from non-customized articles when such articles are manufactured at relatively high speeds.

SUMMARY OF THE INVENTION

The present disclosure involves absorbent articles having customized graphics disposed inside packages labeled as containing customized articles. During the manufacturing process, customized absorbent articles are constructed with article identity graphics, and the packages to contain the customized articles are labeled with package identity graphics. A controller uses article and package identity graphics to track the manufacture of the customized articles and synchronize placement of the customized articles in the appropriately labeled packages. The methods disclosed herein provides for the manufacture of customized absorbent articles in series with the manufacture of absorbent articles having non-custom graphics. The substrates and/or components having the custom graphics in the manufacturing process are detected by a sensor that provides a feedback signal to a controller. The controller, in turn, commands a packing system to place the customized absorbent articles in packages; label the packages with a package identity graphic; and thereby create customized absorbent products.

In one form, a method for producing customized absorbent products includes the steps of: receiving a first order for disposable absorbent articles having custom graphics; printing a first series of custom graphics onto a first substrate, wherein the first series of custom graphics includes the custom graphics from the first order; advancing a second substrate to a converting operation; splicing the first substrate to the second substrate; advancing the first substrate to the converting operation; detecting the first series of custom graphics on the first substrate; converting the first substrate into a first set of custom disposable absorbent articles, wherein the first set of custom disposable absorbent articles includes the first series of custom graphics; labeling a first package with a first package identity graphic, wherein the first package identity graphic identifies the first series of custom graphics; synchronizing the placement of the first set of absorbent articles into the package labeled with the first package identity graphic; splicing a third substrate to the first substrate; and advancing the third substrate to the converting operation.

In another form, a method for producing an absorbent product includes the steps of: providing a first substrate having a plurality of custom graphics printed thereon; advancing the first substrate to a converting operation; detecting the placement of the custom graphics on the first substrate; converting the first substrate into components of disposable absorbent articles having the custom graphics; providing a package; labeling the package with a custom label corresponding with the custom graphics; and synchronizing the placement of the absorbent articles having the custom graphics into the package having the custom label.

In yet another form, a customized absorbent product includes: a package including a custom graphic printed thereon; and a plurality of absorbent articles contained in the package, each of the absorbent articles comprising: a topsheet, a backsheet, and an absorbent core disposed between the topsheet and the backsheet, and wherein the backsheet defines a garment facing surface and a body facing surface and comprises a sheet of film material and a sheet of nonwoven material, wherein the custom graphic is printed directly on the garment facing surface of the sheet of the film material, wherein the nonwoven material is joined with the garment facing surface of the film material, and wherein the custom graphic is visible through the nonwoven material; and wherein the custom graphic is constructed to provide for a selected segregation of the plurality of absorbent articles and a corresponding synchronized placement of the plurality absorbent articles into the package.

BRIEF DESCRIPTION OF THE DRAWINGS

FIG. 1A is a schematic side view of a converting line, substrate, and components.

FIG. 1B is a top view of the substrates and components that corresponds with FIG. 1A.

FIG. 3A is a schematic side view of a converting line, substrate, and components.

FIG. 3B is a top view of the substrates and components that corresponds with FIG. 3A.

DETAILED DESCRIPTION OF THE INVENTION

Figure 2A:
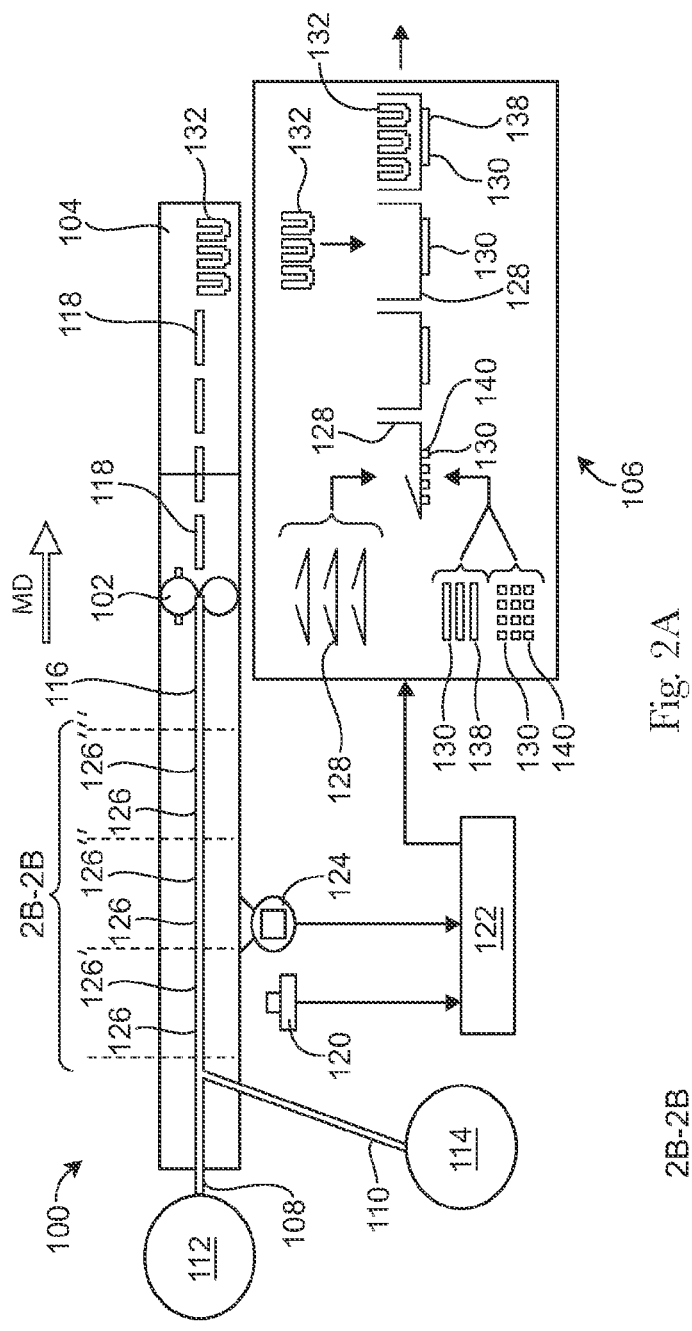
FIG. 2A is a schematic side view of a converting line, substrate, and components.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process. The term "cross direction" (CD) is used herein to refer to a direction that is generally perpendicular to the machine direction.

The term "body facing surface" refers to surfaces of absorbent articles and/or components thereof which face a wearer's body when the absorbent articles are worn, and the term "garment facing surface" refers to surfaces of absorbent articles and/or components thereof that face away from a wearer's body when the absorbent articles are worn. Absorbent articles and components thereof, including the topsheet, backsheet, absorbent core, and any individual materials of their components, have a body facing surface and a garment facing surface.

The term "graphic" refers to images or designs that are constituted by a figure (e.g., a line(s)), a symbol or character, a color difference or transition of at least two colors, or the like. A graphic may include an aesthetic image or design that can provide certain benefit(s) when an absorbent article is viewed. A graphic design is determined by, for example, the color(s) used in the graphic (individual pure ink colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

"Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design.

"Standard" or "standardized" refers to graphics, products, and/or articles that have the same aesthetic appearance without intending to be different from each other.

The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

Aspects of the present disclosure involve customized absorbent products and methods for producing customized absorbent products, and more particularly, absorbent articles having customized graphics disposed inside packages labeled as containing customized articles. During the manufacturing process, customized absorbent articles are constructed with article identity graphics, and the packages to contain the customized articles are labeled with package identity graphics. A controller uses article and package identity graphics to track the manufacture of the customized articles and synchronize placement of the customized articles in the appropriately labeled packages. The methods and products are discussed below in the context of manufacture of absorbent articles constructed from printed substrates or webs. For example, during the manufacture of absorbent articles, printed substrates may be combined with the other substrates and/or discrete components to create a continuous length of absorbent articles. At a downstream portion of the manufacturing process, the continuous length of absorbent articles is subjected to a final knife cut to create separate and discrete absorbent articles. The discrete absorbent articles may be then folded and advanced to a packing system. The packing system receives the absorbent articles and places the absorbent articles in packages. As discussed in more detail below, some printed substrates and/or components may include custom graphics, which in turn, are used to manufacture customized absorbent articles. The methods disclosed herein provides for the manufacture of customized absorbent articles in series with the manufacture of absorbent articles having non-custom graphics. In one embodiment, the substrates and/or components having the custom graphics in the manufacturing process are detected by a sensor that provides a feedback signal to a controller. The controller, in turn, commands the packing system to place the customized absorbent articles in packages; label the packages with a package identity graphic; and thereby create customized absorbent products.

Although the present disclosure is provided in the context of manufacturing absorbent articles, and diapers in particular, it is to be appreciated that the systems and methods disclosed herein may be applied to the manufacture of various types of articles and products involving the monitoring of various different types of substrates and/or components. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets such as the SWIFFER cleaning sheets, pre-moistened wipes or pads such as the SWIFFER WET pre-moistened cloths, paper towels such as the BOUNTY paper towels, dryer sheets such as the BOUNCE dryer sheets and dry-cleaning clothes such as the DRYEL cleaning clothes all sold by The Procter & Gamble Company. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers such as PAMPERS diapers, training and pull-on pants such as PAMPERS FEEL 'N LEARN and EASY UPS, adult incontinence briefs and undergarments such as ATTENDS adult incontinence garments, feminine hygiene garments such as panty liners, absorbent inserts, and the like such as ALWAYS and TAMPAX, toilet paper such as CHARMIN toilet paper, tissue paper such as PUFFS tissue paper, facial wipes or clothes such as OLAY DAILY FACIAL wipes or clothes, toilet training wipes such as KANDOO pre-moistened wipes, all sold by The Procter & Gamble Company. Still other examples of products include packaging components and substrates and/or containers for laundry detergent and coffee, which may be produced in pellets or pouches and may be manufactured in a converting or web process or even discreet products produced at high speed such as high-speed bottling lines or cosmetics. Further, it is to be appreciated that although the present disclosure often refers to monitoring or viewing substrates and/or webs, it is to be appreciated that the methods discussed herein can be used to monitor and/or view combinations of webs and individual components as well as parts added as a continuous web of material and parts added as a discontinuous web of material.

As discussed in more detail below, an absorbent product manufacturing process may include the combination of an absorbent article converting process and a packing system. In one embodiment, the absorbent article converting process may include a converting line or machine configured to manufacture absorbent articles. It is to be appreciated that the systems and methods disclosed herein are applicable to work with various types of converting processes and/or machines. The converting line may be adapted to advance substrates and component materials through the manufacturing process to construct portions of the absorbent articles. The substrates and component parts may be provided as rolls and fed into the converting line. It is to be appreciated that various substrates can be used to construct various components of the absorbent articles, such as backsheets, topsheets, absorbent cores. Exemplary descriptions of absorbent article components are provided below with reference to FIGS. 6 and 7.

As the substrates and components advance through the converting line, the substrates are combined with the other substrates and/or discrete components, to create for example, a continuous length of absorbent articles. At a downstream portion of the converting process, the continuous length of absorbent articles is subjected to a final knife cut to create separate and discrete absorbent articles. The individual articles may also advance to a folder that folds the articles before packaging. As discussed in more detail below, the substrates may include standard and/or custom graphics. As such, the substrates including the custom graphics are used to manufacture custom absorbent articles. The packing system receives and places the folded absorbent articles into packages labeled with package identity graphics. Thus, the packing system may include a plurality of packages and may be adapted to label packages with package identity graphics. It is to be appreciated that the packing system may label the packages with the identify graphics in different ways. For example, the packing system may affix pre-printed labels to the packages. In another scenario, the packing system may print package identify graphics on labels and then affix the labels to the packages. In still another scenario, the packing system may insert the labels inside the packages. In yet another scenario, the packing system may print the identify graphics directly onto the packages. In other configurations, the package may include a label utilizing radio frequency identification (RFID). It is also to be appreciated that the packages may be in various forms, such as for example, bags or boxes, and may be configured to contain one or more absorbent articles.

As discussed in more detail below, as the substrates advance through the converting line, one or more sensors detect article identity graphics on the substrates having custom graphics. In turn, the sensor provides feedback signals to a controller. As the substrates and components travel in the machine direction MD through the converting line, the controller tracks the progress of the substrates and components. As such, the controller tracks the advancement of the custom graphics on the substrate through the converting line. The controller also correlates the substrates with custom graphics with the individual absorbent articles after the final knife. In addition, the controller signals the packing system to label a package with a package identity graphic that corresponds with the article identity graphics on the custom absorbent articles. In turn, the packing system places the custom absorbent articles in correspondingly labeled package to create a custom absorbent product. As such, the process utilizes the article identity graphics and the package identity graphics to provide for a selected segregation of the custom absorbent articles and to provide a corresponding synchronized placement of the plurality absorbent articles into a package.

It is to be appreciated that various types of sensors and other devices may be arranged adjacent the converting line to communicate with the controller. Based on such communications, the controller may monitor and affect various operations on the converting line and packing system. In the methods described herein, the controller may include a computer system. For example, the computer system may include one or more types of programmable logic controller (PLC) and/or personal computer (PC), such as for example, Rockwell PLC or ControlLogix programmable logic controllers, Mitsubishi; Siemens, or any other device capable of receiving inputs from sensors, performing calculations based on those inputs and generating control actions through servomotor controls, electrical actuators or electro-pneumatic, electrohydraulic or other actuators.

It should also be appreciated that various different types of sensors may be used to monitor and detect the article identity graphics on the substrate and/or various components while advancing through the manufacturing process. For example, sensors may be configured to determine the presence or absence of a particular color and/or shape. Particular examples of sensors may include Cognex Insight, Cognex Dataman 100x, various types of commercially available photo-optic sensors that may be adapted to receive either reflected or transmitted light. The sensors can also be configured to communicate with the controller in various ways, such as for example, through a deterministic or non-deterministic communication network, and may be directly connected with the controller to provide analog and/or contact signals.

With respect to the above discussion, it is also to be appreciated that the article identity graphics and the package identity graphics may be configured in different ways. For example, article identity graphics and/or package identity graphics may include bar codes, alphanumeric characters, colors, and/or shapes. In addition, the custom graphics may also function as the article identity graphics and the package identity graphics. In other words, the article identity graphics and the package identity graphics may be one in the same as the custom graphics. Further, in some embodiments, the article identity graphic and the package identity graphic may be identical. For example, the article identity graphic of a customized absorbent article may be in the form of the custom graphic, and the package identity graphic of the package to contain the custom absorbent articles may identical to the article identity graphic (i.e. the custom graphic). In other embodiments, the article identity graphic and the package identity graphic may be different, so long as the controller is able to correlate and synchronize the two identity graphics. For example, the article identity graphic of a customized absorbent article may be in the form of the custom graphic, and the package identity graphic may be in the form of a bar code and vice versa. In some embodiments, the package may be made from transparent material or may include a transparent window so that article identity graphic can be viewed from outside other package. In such a configuration, the article identity graphic may function as the package identity graphic.

Figure 2C:
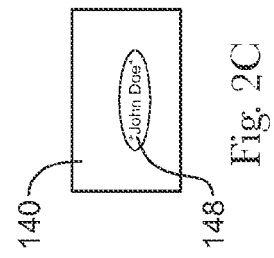
FIG. 2C is a top view of a package label with a package identity graphic from FIG. 2A.
Figure 2B:
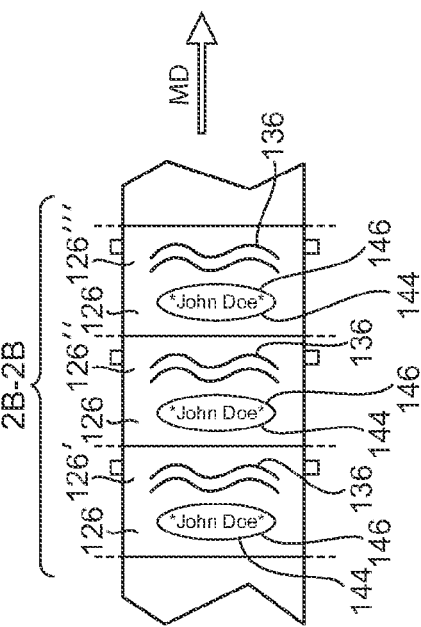
FIG. 2B is a top view of the substrates and components that corresponds with FIG. 2A.

To provide additional context to the above discussion, the following provides a detailed description of one example implementation of an absorbent product manufacturing process that includes the combination of an absorbent article converting process and a packing system. In particular, FIGS. 1A, 2A, and 3A show schematic side views of a converting line 100 with substrates and components advancing along the machine direction MD to a final knife 102, a folder 104, and a packing system 106. FIGS. 1B, 2B, and 3B show a top view of substrates and graphics that correspond with FIGS. 1A, 2A, and 3A, respectively. For the purposes of the discussion relating to FIGS. 1A-3B, the converting line 100 is described in the context of a diaper converting line. The converting line 100 may include one or more motors that drive transport systems to move diaper substrates and component materials through the manufacturing process. For example, FIGS. 1A, 2A, and 3A show a first substrate 108 of material and a second substrate 110 of material used to construct portions of the diapers. The substrates may be provided as rolls 112, 114 and fed into the converting line 100. As the first substrate 108 advances through the converting line 100, the first substrate 108 is combined with other substrates and/or discrete components, such as for example, the second substrate 110, to create a continuous length of absorbent articles 116. At a downstream portion of the converting process, the continuous length of absorbent articles 116 is cut by the final knife 102 to create individual diapers 118. The individual diapers 118 may then advance to the folder 104 that folds the diapers 118 before packaging. As discussed in more detail below, the first substrate 108 and/or second substrate 110 may include custom graphics. As such, the first and/or second substrates including the custom graphics are used to manufacture custom absorbent articles. As shown in FIGS. 1A, 2A, and 3A, the first substrate 108 and the second substrate 110 are shown to enter and advance in the machine direction MD through the converting line 100. FIGS. 1A, 2A, and 3A also show a sensor 120, controller 122, a machine axis 124, final knife 102, and folder 104 associated with the converting line 100. The machine axis 124 is shown as an example device that provides substrate position and speed feedback signals to the controller 122. In turn, the controller utilizes the machine axis feedback to divide the substrates into virtual articles 126 along the machine direction MD. For the purposes of the present description, FIGS. 1A-3B show only three virtual articles 126', 126", 126''' having lengths in the machine direction that correspond with the pitch lengths of the individual diapers 118 being produced. FIGS. 1A-3B show the advancement of the first substrate 108 and second substrate 110 in the machine direction past the sensor 120, which can be configured to detect various types of graphics. As discussed in more detail below with reference to FIGS. 1A-3B, the second substrate 110 is bonded to the first substrate 108 to form an absorbent article component, such as for example, a backsheet of a diaper, wherein the first substrate may include standard graphics, and the second substrate may selectively include custom graphics.

The packing system 106 shown in FIGS. 1A, 2A, and 3A includes a plurality of packages 128 and a plurality of labels 130. The packing system 106 affixes the labels 130 to the packages 128 and inserts one or more folded articles 132 into respective packages. It is to be appreciated that the packages 128 may be in various forms, such as bags or boxes, and may be configured to contain one or more absorbent articles. As discussed in more detail below, the sensor 120 detects substrates including custom graphics as the substrates advance through the converting line 100. The sensor 120 provides feedback signals to the controller 122. As the substrates and components travel in the machine direction MD through the converting line 100, the controller tracks the progress of the substrates and components. As such, the controller tracks the advancement of the custom graphics on the substrate through the converting line. The controller also correlates the locations of the custom graphics on virtual articles 126 with the individual diapers 132 after the final knife 102. In addition, the controller 122 signals the packing system 106 to affix a label 130 having a package identity graphic to a package 128 that is to contain the custom diapers. In turn, the packing system 106 places the custom diapers in the custom coded package to create a custom absorbent product 134, such as shown for example in FIG. 5E.

FIGS. 1A and 1B show the continued advancement of the first substrate 108 and second substrate 110 in the machine direction MD, and in particular, advancement of standard graphics 136 on three virtual articles 126', 126", 126''' past the sensor 120. As shown in FIG. 1B, the standard graphic 136 is shown as being identical on each product, and is shown as a pair of curved lines. It is to be appreciated that the illustrated standard graphic 136 is shown as an example, and various different types of graphics may be used. FIG. 1A also shows the packing system including a plurality of packages 128 and labels 130. In particular, the packing system includes a plurality of standard labels 138 and custom labels 140. The packing system 106 in FIG. 1A affixes the labels 130 to the packages 128 and appropriately aligns the packages 128 to receive folded articles 132 from the converting line 100. As shown in FIG. 1A, folded articles 132 with standard graphics 136 are inserted into packages 128 with standard labels 138 to create standard absorbent products 142.

Next, FIGS. 2A and 2B show the continued advancement from FIGS. 1A and 1B of the first substrate 108 and second substrate 110 in the machine direction MD, and in particular, advancement of three virtual articles 126', 126", 126''' including custom graphics 142 past the sensor 120. As shown in FIG. 2B, the custom graphics 142 are depicted as personalized graphics in the form of a person's name and are located adjacent the standard graphics 136. In FIG. 2A, the sensor 120 detects article identity graphics 146 on the virtual articles 126', 126", 126''' and provides feedback to the controller 122 that virtual articles with customized graphics 144 have been detected. In the example of FIG. 2A, the article identity graphics 146 are the custom graphics 144 (e.g. the person's name). Although the custom graphics 144 shown in FIG. 2B are also used as the article identity graphics 146, it is to be appreciated that the article identity graphics can be different from the custom graphics. Once the article identity graphics 146 have been detected, the controller 122 provides a command signal to the packing system 106 to affix a custom label 140 to a package 128, which will contain the customized articles. The custom label 140 affixed to the package 128 includes a package identity graphic 148 that corresponds with the article identity graphics 146. For example, as shown in FIG. 2C, the package identity graphic 148 may the same as the article identity graphic 146 (e.g. the person's name).

FIGS. 3A and 3B show the continued advancement from FIGS. 2A and 2B of the first substrate 108 and second substrate 110, as well as individual customized articles 150 made from the virtual articles 126', 126", 126''' with the custom graphics 144 having been subjected to the final knife 102. In particular, FIG. 3A shows a custom absorbent product 134 with the deposition of the customized individual diapers 150 into the package 128 including the custom label 140 with the package identity graphic 148. In addition, FIGS. 3A and 3B show the resumed production of articles with standard graphics 136 without custom graphics 144.

Figure 4A:
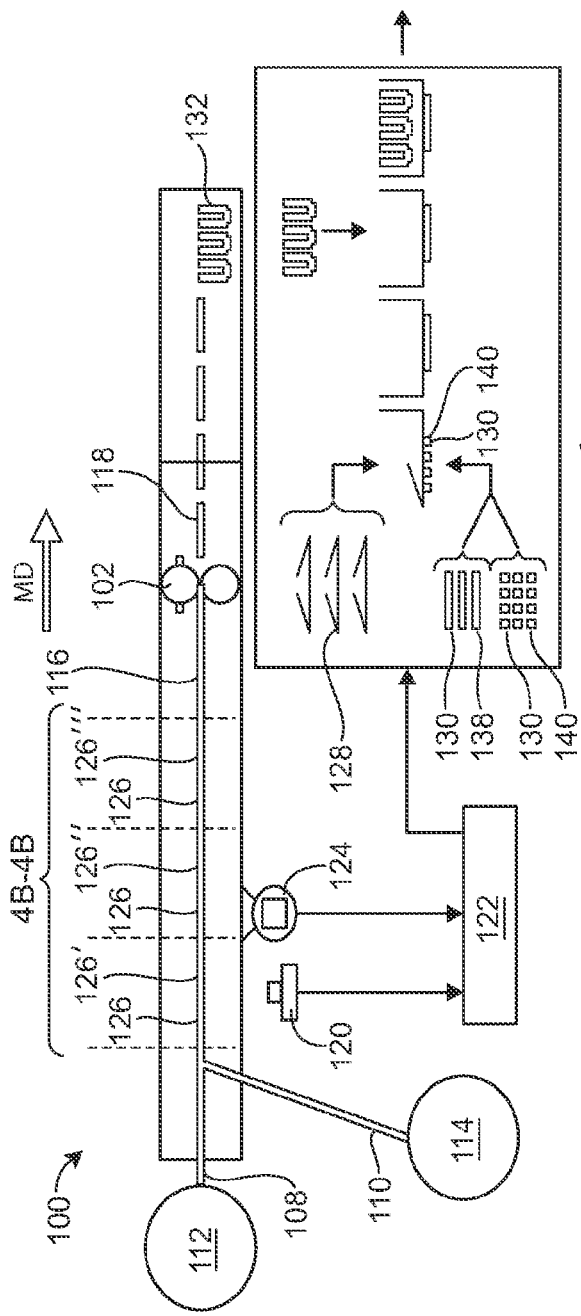
FIG. 4A is a schematic side view of a converting line, substrate, and components.
Figure 4B:
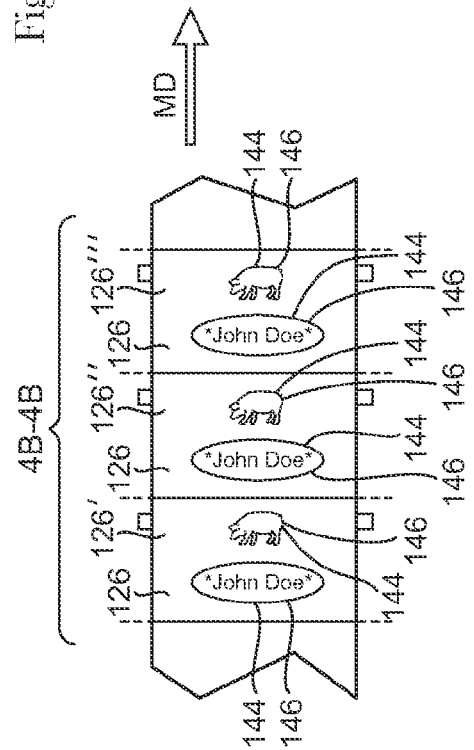
FIG. 4B is a top view of the substrates and components that corresponds with FIG. 4A.
Figure 4C:
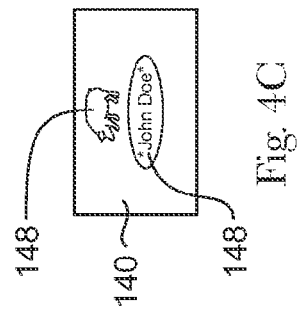
FIG. 4C is a top view of a package label with a package identity graphic from FIG. 4A.

It is to be appreciated that customized absorbent products 134 may include packages 128 with custom labels 140 and contain one or more customized absorbent articles 150. The customized absorbent articles 150 may include custom graphics 144 that may be identical to or different from each other. In addition, the custom graphics 144 may be stand-alone graphics or comprise component parts of other graphics. Further, the methods and products describe herein may utilize various combinations of graphics and methods for printing such graphics, for example, as are described in U.S. Patent Publication Nos. 2005/0217791 A1 and 2004/0143231 A1. For example, FIGS. 4A and 4B show a manufacturing scenario wherein the virtual articles 126', 126", 126''' include custom graphics 144 in the form of a farm animal (e.g. a pig) and a person's name. As such, the farm animal may be a graphic that can be selected by a purchaser from sets or categories of graphic offered by a manufacturer. For example, a manufacturer may offer graphics from various categories, such as farm animals, nursery rhymes, cartoon characters, automobile depictions, and the like, wherein purchasers can have custom articles created with graphics selected from the manufacturer's offered categories. In addition, custom graphics can include a person's name or other personalized insignia, which may be requested by a purchaser from the manufacturer to create custom articles with personalized graphics. Also, as shown in FIG. 4B, the custom graphic 144 also functions as the article identity graphic 146. FIG. 4C also shows an example of a package identity graphic 148 on a custom label 140 that corresponds with the custom graphics 144.

Expanding on the above discussion as well as FIGS. 1A-4B, it is to be appreciated that the custom graphics can be printed on substrates used to construct various components of customized absorbent articles. FIGS. 5A-5E show one example of how the first substrate 108 and second substrate 110 referred to in FIGS. 1A-4B may be used in the manufacture of a customized absorbent product 134, and in particular, the manufacture backsheets of customized absorbent articles 150. Specifically, the first substrate 108 and second substrate 110 are joined to form a laminate used in the manufacture of a diaper backsheet. The first substrate 108 includes a repeating series of graphics G1-Gn. Although the repeating series of graphics is referred to with reference to FIGS. 5A-5E as standard graphics 136, it is to be appreciated that the repeating graphics may be custom graphics. The second substrate 110 may be adapted to include custom graphics 144. As discussed in more detail below, the second substrate 110 having custom graphics 144 printed thereon can be inserted or spliced into the converting line 100 and be combined with the first substrate 108 to manufacture custom absorbent articles 150.

Figure 5A:
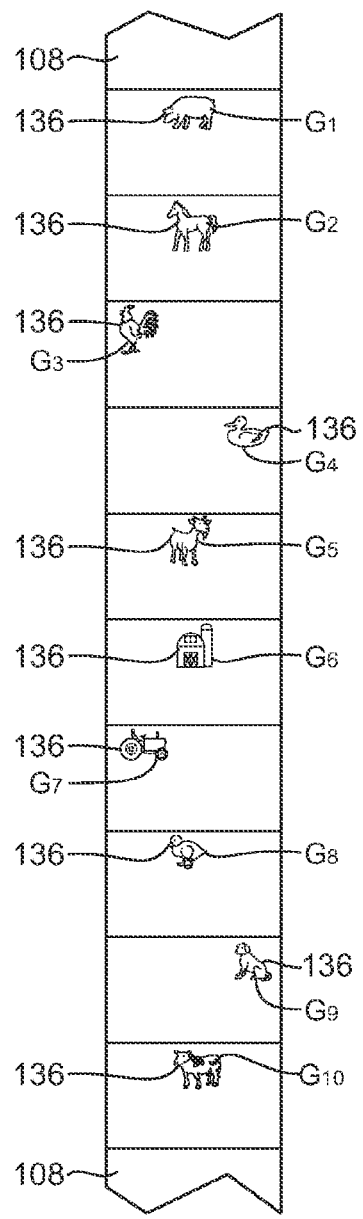
FIG. 5A is a top view of a first substrate with a series of graphics printed on a garment facing surface.
Figure 5B:
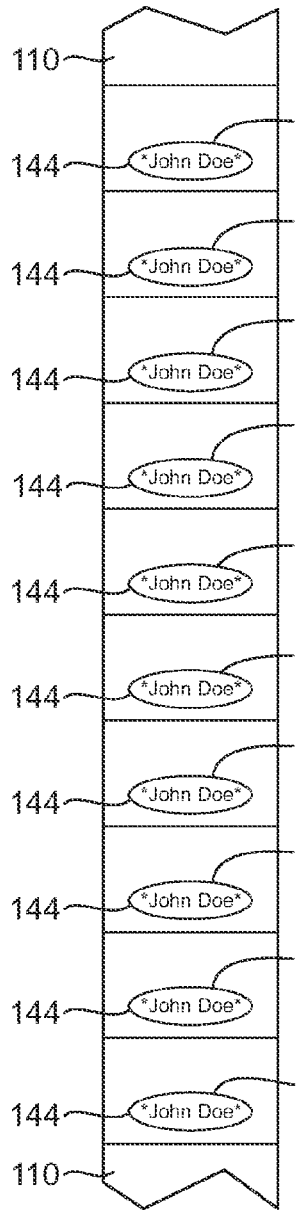
FIG. 5B is a top view of a second substrate with custom graphics printed on a garment facing surface.

FIG. 5A shows an example of the first substrate 108 printed with standard graphics 136 in the form of a repeating series of 10 different graphics (G1-G10) in the MD direction. Various embodiments of such repeating series of different graphics is described in U.S. patent application Ser. No. 12/249,153, filed on Oct. 10, 2008, and entitled "Absorbent Articles Having Distinct Graphics and Apparatus and Method for Printing Such Absorbent Articles." FIG. 5B shows an example of the second substrate 110 printed with custom graphics 144 in the form of a series of 10 custom graphics (CG1-CG10) in the MD direction. The first substrate 108 may be in the form of a nonwoven outer cover material, and the second substrate 110 may be in the form of a liquid impervious film material. Specific examples of such materials are provided below with reference to FIGS. 6 and 7. During the manufacture of absorbent products as described above with reference to FIGS. 1A-4B, the first substrate 108 may be joined to the second substrate 110 to form a laminate, which in turn, may be used to manufacture the backsheet of a customized diaper 150. In particular, FIG. 4C shows a laminate 152 formed by joining the first substrate 108 of FIG. 5A with the second substrate 110 of FIG. 5B. Specifically, the first substrate 108 is placed on top of the second substrate 110 such that the custom graphics 144 printed on the second substrate 110 are covered by and visible through the first substrate 108.

Figure 5C:
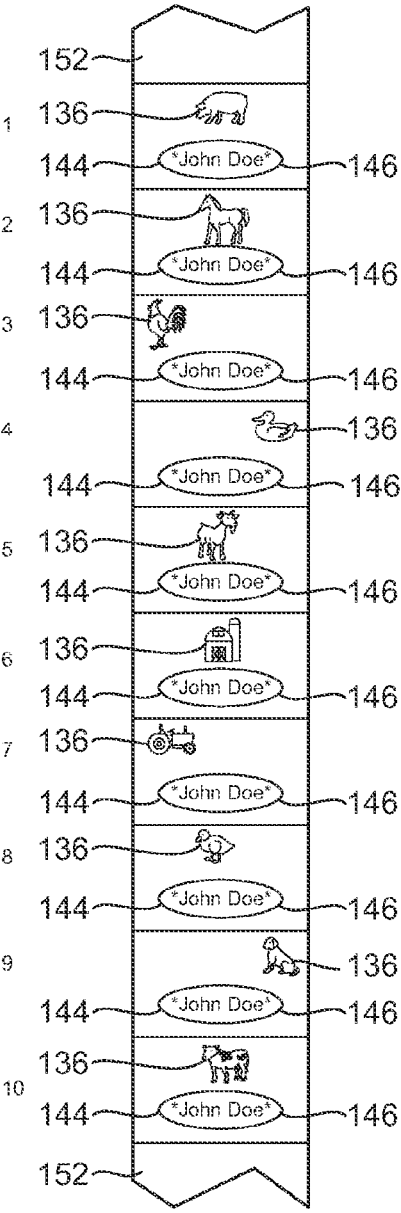
FIG. 5C is a top view of the first substrate joined to the garment facing surface of the second substrate.

Although the graphics 136 shown in FIGS. 5A and 5C are different from each other, it is to be appreciated that the graphics may be identical and may be of a series having more or less than 10. In addition, although the custom graphics 144 shown in FIGS. 5B and 5C are the same, it is to be appreciated that the custom graphics 144 may be configured differently from each other. Further, in the example embodiment discussed with reference to FIGS. 5A-5E, the custom graphics 144 also function as article identity graphics 146. As previously discussed, it is to be appreciated that the article identity graphics 146 may be a separate graphic, as discussed above, such as for example, a code, symbol, and/or shape.

Figure 5D:
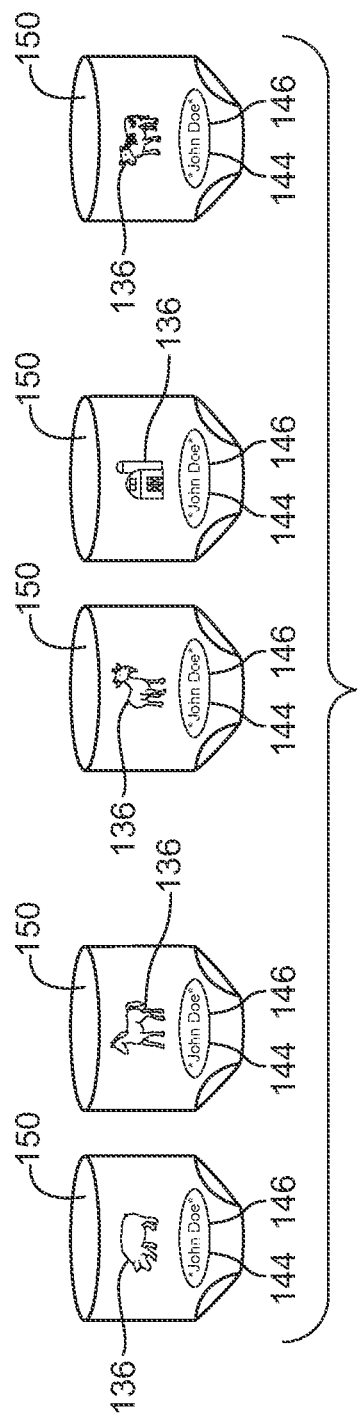
FIG. 5D is a set of customized absorbent articles.
Figure 5E:
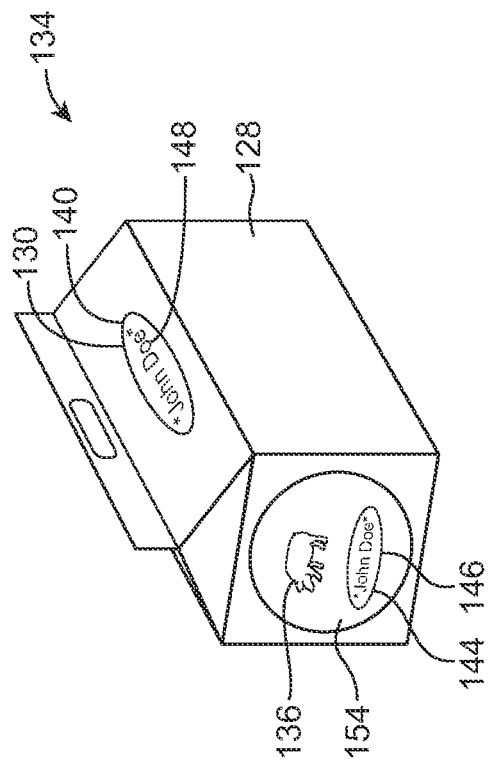
FIG. 5E is a customized absorbent product.

As mentioned above, the methods discussed herein may be utilized to efficiently manufacture customized absorbent articles 150 in series with non-customized absorbent articles. For example, orders for customized absorbent articles may be received, and in response to such orders, substrates used to manufacture absorbent articles may be printed with custom graphics 144 that also function as or with additional article identity graphics 146 off-line. For example, upon receipt of an order from a customer for customized absorbent articles, a manufacturer can print a length of the second substrate with custom graphics and article identity graphics, such as shown in FIG. 5B. Also in response to the order, a package label 130, 140 having a package identity graphic 148 may be printed, such as shown in FIG. 5E. The package identity graphic 148 is associated with the identification of the custom graphics 144 and/or article identity graphics 146. The process of printing custom graphics 144 and article identity graphics 146 on the second substrate 110 and custom printing package labels 140 associated therewith is repeated until a desired length of the second substrate 110 is printed.

Next, the second substrate 110 having the custom graphics 144 and article identity graphics 146 printed thereon may be spliced into a converting line and used to manufacture sets of customized absorbent articles corresponding with received orders. For example, the length of substrate 110 having the custom graphics 144 shown in FIG. 5B may be used to manufacture a set of customized absorbent articles 150 such as shown in FIG. 5D. As discussed above with reference to FIGS. 1-4B, the sensor 120 detects the article identity graphics 146 and the controller 122 commands the packing system 106 to affix the corresponding package labels 140 onto the packages 128 adapted to contain the custom absorbent articles 150. The custom absorbent articles 150 are then placed in an appropriately labeled package 128 to create a customized absorbent product 134, such as shown in FIG. 5E. The package 128 shown in FIG. 5E also includes a transparent window 154 therein such that the custom graphic 144 on the absorbent articles 150 contained therein can be viewed from outside the package. The process continues until the second substrate 110 with the custom graphics 144 is completely used. At which point, another second substrate with or without custom graphics can be spliced thereto for uninterrupted manufacture of absorbent articles.

It is to be appreciated that the graphics 136, 144, 146 discussed herein may be printed in various ways. Printing may be characterized as an industrial process in which an image is reproduced on a substrate, such as paper, polyolefin film, or nonwoven fabric. There are various classes of printing processes, which may include stencil and screen printing, relief printing, planographic printing, intaglio printing, and electronic printing. Stencil and screen printing may be used for printing T-shirts, signage, banners, billboards, and the like. Examples of relief printing may include letterpress and flexography. Examples of planographic printing may include offset lithography, screenless lithography, collotype, and waterless printing. In addition, examples of intaglio printing may include gravure, steel-die, and copper-plate engraving. Examples of electronic printing may include electrostatic, magnetographic, ion or electron deposition, and ink-jet printing. It is it to be appreciated that various types of printing processes may be used to create the graphics disclosed herein. For example, in some embodiments, flexography may be used. In particular, flexography may utilize printing plates made of rubber or plastic with a slightly raised image thereon. The inked plates are rotated on a cylinder which transfers the image to the substrate. Flexography may be a relatively high-speed print process that uses fast-drying inks. In addition, flexography can be used to print continuous patterns on many types of absorbent and non-absorbent materials. Other embodiments may utilize gravure printing. More particularly, gravure printing utilizes an image etched on the surface of a metal plate. The etched area is filled with ink and the plate is rotated on a cylinder that transfers the image to the substrate. Still other embodiments may utilize ink jetprinting. Ink jet is a non-impact dot-matrix printing technology in which droplets of ink are jetted from a small aperture directly to a specified position on a media to create an image. Two examples of inkjet technologies include thermal bubble or bubble jet and piezoelectric. Thermal bubble uses heat to apply to the ink, while piezoelectric uses a crystal and an electric charge to apply the ink.

Figure 6:
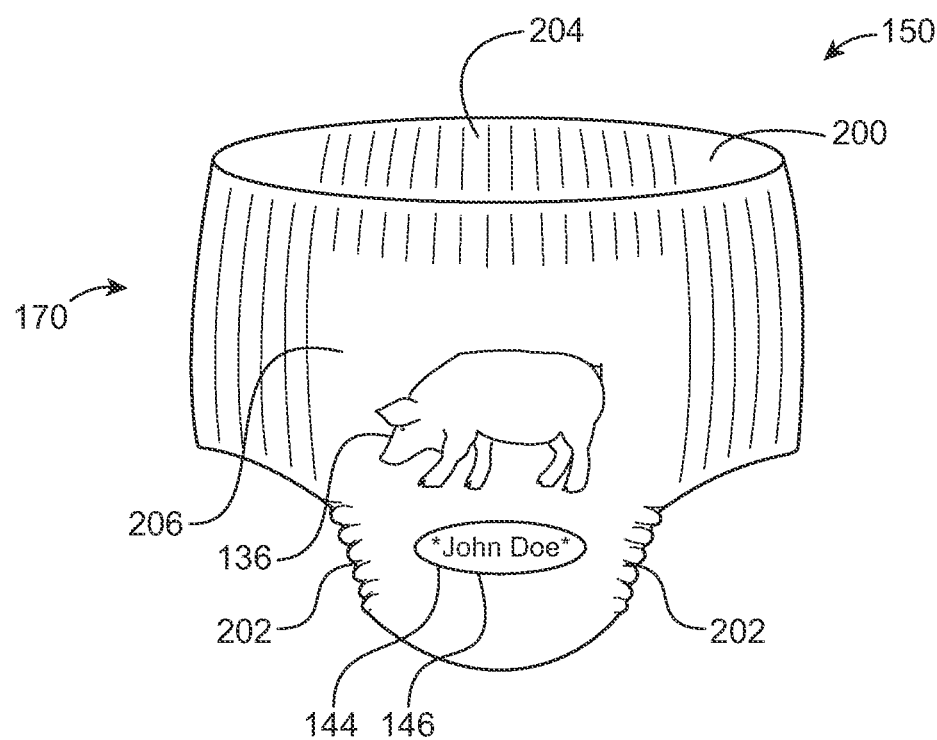
FIG. 6 is a perspective view an absorbent article.
Figure 7:
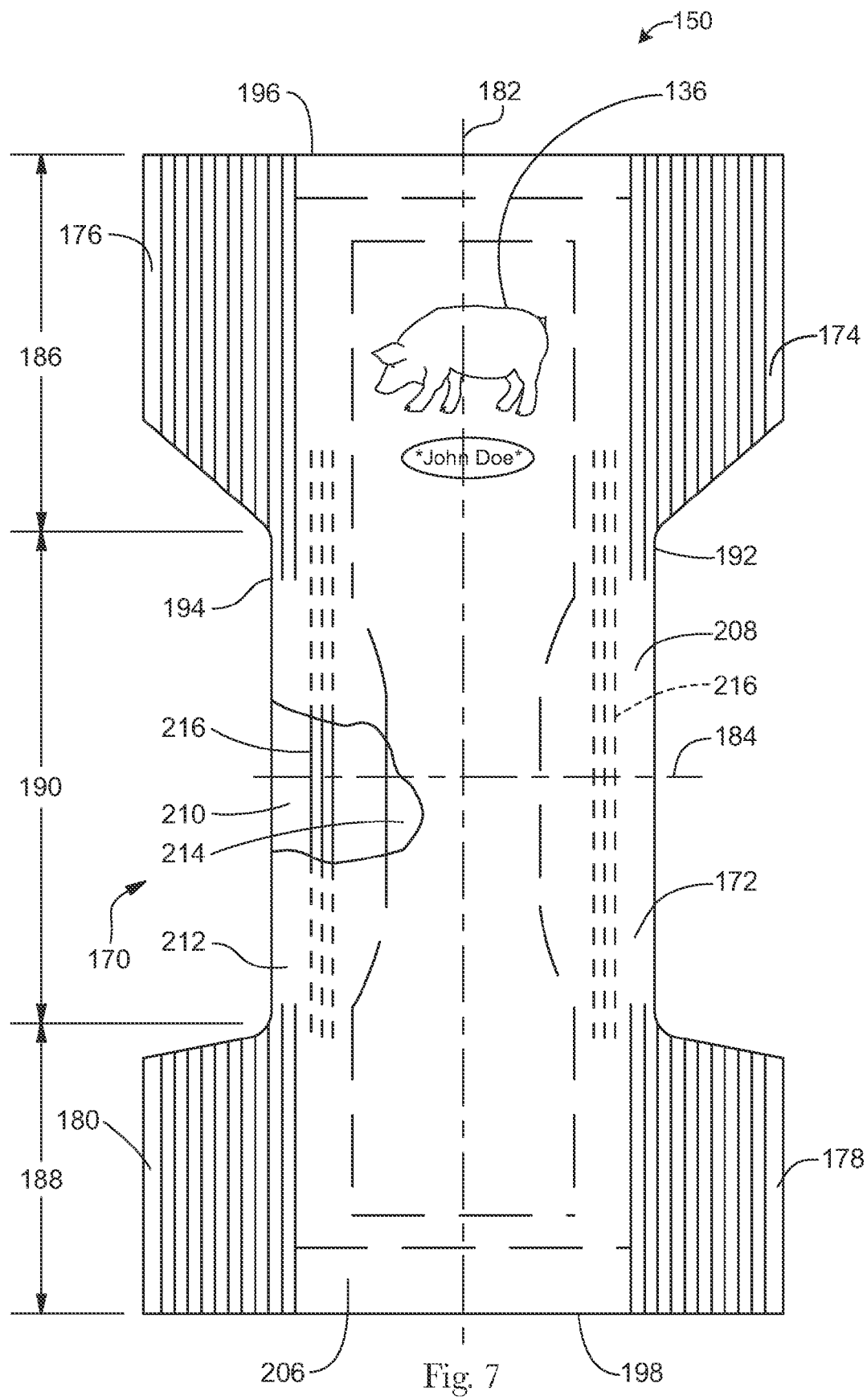
FIG. 7 is a partially cut away plan view of the absorbent article shown in FIG. 5.

The customized absorbent products 134 may also include various types of absorbent articles 150. For example, the absorbent product 134 shown in FIG. 5E includes a plurality of diapers. As mentioned above, the diapers may include printed components with custom graphics printed thereon. For the purposes of a specific illustration, FIGS. 6 and 7 shows one example of a customized disposable absorbent article 150 in the form of a custom diaper 170 which may be contained in the package 128 shown in FIG. 5E. FIG. 7 is a plan view of the diaper 170 including a chassis 172 shown in a flat, unfolded condition, with the portion of the diaper that faces away from a wearer oriented towards the viewer. A portion of the chassis structure is cut-away in FIG. 7 to more clearly show the construction of and various features that may be included in embodiments of the diaper.

As shown in FIGS. 6 and 7, the diaper 170 includes a 172 chassis having a first ear 174, a second ear 176, a third ear 178, and a fourth ear 180. To provide a frame of reference for the present discussion, the chassis 172 is shown with a longitudinal axis 182 and a lateral axis 184. The chassis 172 is shown as having a first waist region 186, a second waist region 188, and a crotch region 190 disposed intermediate the first and second waist regions. The periphery of the diaper is defined by a pair of longitudinally extending side edges 192, 194; a first outer edge 196 extending laterally adjacent the first waist region 186; and a second outer edge 198 extending laterally adjacent the second waist region 188. As shown in FIG. 7, the diaper 170 has a waist opening 200 and two leg openings 202. The diaper 170 may also be provided in the form of a pant-type diaper or may alternatively be provided with a re-closable fastening system, which may include fastener elements in various locations to help secure the diaper in position on the wearer. For example, fastener elements may be located on the ears and may be adapted to releasably connect with one or more corresponding fastening elements located in the first or second waist regions.

As shown in FIGS. 6 and 7, the chassis includes an inner, body facing surface 204, and an outer, garment facing surface 206. As shown in FIG. 7, the chassis 172 may include an outer covering layer including a topsheet 210 and a backsheet 212. An absorbent core 214 may be disposed between a portion of the topsheet 210 and the backsheet 212. It is to be appreciated that any one or more of the regions of the chassis may be stretchable and may include various types of elastomeric materials and/or laminates. As such, the diaper may be configured to adapt to a specific wearer's anatomy upon application and to maintain coordination with the wearer's anatomy during wear.

Embodiments of the diaper may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. Nos. 5,514,121; 5,171,236; 5,306,266; 5,397,318; 5,540,671; and PCT Application WO 93/25172; which are all hereby incorporated by reference herein. Examples of compartments or voids are disclosed in U.S. Pat. Nos. 4,968,312; 4,990,147; 5,062,840; 6,482,191; and 5,269,755, which are all hereby incorporated by reference herein. Examples of suitable transverse barriers are described in U.S. Pat. Nos. 5,554,142 and 5,653,703; and PCT Patent Publication WO 94/14395, which are all hereby incorporated by reference herein. All of the above-cited references are hereby incorporated by reference herein. In addition to or in place of the voids, pockets and barriers, described above, embodiments of the absorbent article may also include a waste management element capable of effectively and efficiently accepting, storing and/ or immobilizing viscous fluid bodily waste, such as runny feces, such as described in U.S. Pat. No. 6,010,491, which is hereby incorporated by reference herein.

As previously mentioned, the chassis 172 may include the backsheet 212, shown for example, in FIG. 7. In some embodiments, the backsheet is configured to prevent exudates absorbed and contained within the chassis from soiling articles that may contact the diaper, such as bedsheets and undergarments. Some embodiments of the backsheet may be fluid permeable, while other embodiments may be impervious to liquids (e.g., urine) and comprises a thin plastic film. Some backsheet films may include those manufactured by Tredegar Industries Inc. of Terre Haute, Ind. and sold under the trade names X15306, X10962, and X10964. Other backsheet materials may include breathable materials that permit vapors to escape from the diaper while still preventing exudates from passing through the backsheet. Exemplary breathable materials may include materials such as woven webs, nonwoven webs, composite materials such as film-coated nonwoven webs, and microporous films. Suitable breathable composite materials are described in greater detail in PCT Application No. WO 95/16746, published on Jun. 22, 1995 in the name of E. I. DuPont and U.S. Pat. No. 5,865,823, both of which are hereby incorporated by reference herein. Other breathable backsheets including nonwoven webs and apertured formed films are described in U.S. Pat. Nos. 5,571,096 and 6,573,423, which are all hereby incorporated by reference herein.

The backsheet 212 may be formed by only one sheet (or layer) material such as a breathable (or microporous) film material or a non-breathable (or non-microporous) film material. In some embodiments, the backsheet may be formed by two (or more) sheet (or layer) materials which may include a non-breathable (or breathable) film material and a nonwoven outer cover material. In some embodiments, the backsheet may be formed by a laminate of two sheet (or layer) materials joined together, for example, the backsheet may include a non-breathable film material and a nonwoven material which is joined to the garment facing surface of the film material to provide a cloth-like and/or garment-like feel. In accordance with the discussion above, graphics may be printed on a substrate to make printed component material, which may be converted into printed components to manufacture the backsheet. Thus, the substrate may be in the form of a film material and/or nonwoven material used to construct the backsheet. As such, graphics G may be printed on any surface of the component material(s) of the backsheet. For example, graphics can be printed on any of the garment facing surfaces and the body facing surfaces of the film material and the nonwoven material. In some embodiments, graphics are printed directly on the nonwoven material. In other embodiments, the graphic G is printed on the garment facing surface of the film material. In such an arrangement, graphics may be covered (or protected) by the nonwoven material, wherein the graphics are visible through the nonwoven material.

As with the backsheet 212, graphics may be printed on a substrate used as a printed component material to construct the topsheet 210. As such, graphics G may be printed on any surface of the component material(s) of the topsheet. All or at least a portion of the topsheet may be liquid pervious, permitting liquid to readily penetrate therethrough. As such, the topsheet may be manufactured from a wide range of materials, such as porous foams; reticulated foams; apertured nonwovens or plastic films; or woven or nonwoven webs of natural fibers (e.g., wood or cotton fibers), synthetic fibers (e.g., polyester or polypropylene fibers), or a combination of natural and synthetic fibers. One example of a topsheet including a web of staple length polypropylene fibers is manufactured by Veratec, Inc., a Division of International Paper Company, of Walpole, Mass. under the designation P-8. Examples of formed film topsheets are described in U.S. Pat. Nos. 3,929,135; 4,324,246; 4,342,314; 4,463,045; and 5,006, 394, all of which are hereby incorporated by reference herein. Other topsheets may be made in accordance with U.S. Pat. Nos. 4,609,518 and 4,629,643, both of which are hereby incorporated by reference herein.

In some embodiments, the topsheet is made of a hydrophobic material or is treated to be hydrophobic in order to isolate the wearer's skin from liquids contained in the absorbent core. If the topsheet is made of a hydrophobic material, at least the upper surface of the topsheet may be treated to be hydrophilic so that liquids will transfer through the topsheet more rapidly. The topsheet can be rendered hydrophilic by treating it with a surfactant or by incorporating a surfactant into the topsheet. A more detailed discussion of such a treatment and hydrophilicity is contained in U.S. Pat. Nos. 4,988, 344 and 4,988,345, all of which are hereby incorporated by reference herein. A more detailed discussion of some methods for incorporating surfactant in the topsheet can be found in U.S. Statutory Invention Registration No. H1670, which was published on Jul. 1, 1997, in the names of Aziz et al., all of which are hereby incorporated by reference herein. In some embodiments, the topsheet 788 may include an apertured web or film that is hydrophobic. This may be accomplished eliminating the hydrophilizing treatment step from the production process and/or applying a hydrophobic treatment to the topsheet, such as a polytetrafluoroethylene compound like SCOTCHGUARD or a hydrophobic lotion composition, as described below. A more detailed discussion of various apertured topsheets can be found in U.S. Pat. Nos.

5,342,338; 5,941,864; 6,010,491; and 6,414,215, all of which are hereby incorporated by referenced herein.

The absorbent core 214 may include components such as an acquisition layer and absorbent material that is generally compressible, conformable, non-irritating to the wearer's skin, and capable of absorbing and retaining liquids such as urine and other body exudates. Thus, in addition to backsheet and topsheet components, it should be appreciated that graphics may be printed on substrates used as printed component material to construct the absorbent core and acquisition layer. In addition, graphics G may be printed on any surface of various component material(s) of the absorbent core. The absorbent core can also be manufactured in a wide variety of sizes and shapes (e.g., rectangular, hourglass, T-shaped, asymmetric, etc.). The absorbent core may also include a wide variety of liquid-absorbent materials commonly used in disposable diapers and other absorbent articles. In one example, the absorbent core includes comminuted wood pulp, which is generally referred to as airfelt. Examples of other absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

It is to be appreciated that the configuration and construction of the absorbent core may be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). Exemplary absorbent structures are described in U.S. Pat. Nos. 4,610,678; 4,673,402; and 4,834,735; 4,888,231; 5,137,537; 5,147,345; 5,342,338; 5,260,345; 5,387,207; and 5,650,222, all of which are hereby incorporated by reference herein.

The absorbent core may also have a multiple layered construction. A more detailed discussion of various types of multi-layered absorbent cores can be found in U.S. Pat. Publication Nos. 2004/0162536A1 and 2004/0167486A1; U.S. Pat. Nos. 5,669,894; 6,441,266; 5,562,646; European Pat. No. EP0565606B1; PCT Publication No. WO 2006/015141, which are all hereby incorporated by reference herein. In some embodiments, the absorbent article includes an absorbent core that is stretchable. In such a configuration, the absorbent core may be adapted to extend along with other materials of the chassis in longitudinal and/or lateral directions. The absorbent core can also be connected with the other components of the chassis various ways. For example, the diaper may include a "floating core" configuration or a "bucket" configuration wherein the diaper includes an anchoring system that can be configured to collect forces tending to move the article on the wearer. Such an anchoring system can also be configured to anchor itself to a body of a wearer by contacting various parts of the body. In this way, the anchoring system can balance the collected moving forces with holding forces obtained from the anchoring. By balancing the collected moving forces with the obtained holding forces, the anchoring system can at least assist in holding the disposable wearable absorbent article in place on a wearer.

The diapers according to the present disclosure can also include other features such as elastically extensible side panels. The side panels may be joined at seams to form the waist opening and the leg openings. The diapers may also includes leg elastics 216, such as shown in FIG. 8, and an elastic waist region to enhance the fits around the legs and waist of the wearer. Example leg elastic and leg cuff embodiments are disclosed in, for example, U.S. Pat. Nos. 4,695,278 and 4,795,454.

In addition to the backsheet, topsheet, absorbent core, acquisition layer, and other diaper components, graphics may also be printed on substrates used as printed component material to construct the fastening elements on the diaper, such as for example, a landing zone. Depending on the particular configuration, it is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274, which are all hereby incorporated by reference herein. Additional examples of fasteners and/or fastening elements are discussed in U.S. Pat. Nos. 6,482,191; 6,251,097; and 6,432,098, which are all hereby incorporated by reference herein. Other fastening systems are described in more detail in U.S. Pat. Nos. 5,595,567; 5,624,427; 5,735,840; and 5,928,212, which are all hereby incorporated by reference herein. The fastening system may also provide a means for holding the article in a disposal configuration as disclosed in U.S. Pat. No. 4,963,140, which is hereby incorporated by reference herein.

The foregoing description of the diaper shown in FIGS. 6 and 7, illustrate that a repeating series of graphics G1-Gn may be printed according to the methods and apparatuses disclosed herein on substrates, which may be referred to as component graphic material, to construct various components, such as for example, backsheets, topsheets, absorbent cores, acquisition layers, landing zones, and other fastening elements. In addition, the graphics may be printed on the body facing surface, the garment facing surface, or both surfaces of such components.

As previously mentioned, in some embodiments of the absorbent product, the graphics G1-Gn on the absorbent articles are different from each other in terms of graphic design. Herein, "different in terms of graphic design" means that graphics are intended to be different when viewed by users or consumers with normal attentions. Thus, two graphics having a graphic difference(s) which are unintentionally caused due to a problem(s) or an errors) in a manufacture process, for example, are not different from each other in terms of graphic design. The graphic design is determined by, for example, the color(s) used in the graphic (individual pure ink colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

It should be appreciated that although a package may contain absorbent articles which have the graphics G1-Gn different from each other, the package may also contain, if desired, one or more additional absorbent article(s) which has a graphic that is the same as one the other graphics in the package. In other words, the absorbent product may include at least n absorbent articles, in a series, which have the graphics G1-Gn different from each other, and can include an additional absorbent article(s) each having the same graphic(s).

It should be appreciated that printed graphics may be other types that are permanent or active graphics. Active graphics are graphics that are configured to appear or disappear upon various types of triggering mechanisms or stimuli, such as for example, moisture (e.g. aquachromic ink graphics), temperature change (e.g. thermochromic ink graphics), and/or light (e.g. photochromic ink graphics, UV or IR light).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for producing customized absorbent products comprising the steps of:
   advancing a first substrate to a converting operation;
   advancing a first length of a second substrate to the converting operation;
   receiving a first order for disposable absorbent articles having custom graphics;
   printing a first series of custom graphics onto a second length of the second substrate, wherein the first series of custom graphics includes the custom graphics from the first order;
   splicing the second length of the second substrate to the first length of the second substrate;
   combining the first length of the second substrate with the advancing first substrate in the converting operation;
   subsequently combining the spliced second length of the second substrate with the advancing first substrate in the converting operation;
   detecting the first series of custom graphics on the second length of the second substrate;
   converting the combined first length of the second substrate and first substrate into disposable absorbent articles;
   subsequently converting the combined second length of the second substrate and first substrate into a first set of custom disposable absorbent articles, wherein the first set of custom disposable absorbent articles includes the first series of custom graphics;
   labeling a first package with a first package identity graphic, wherein the first package identity graphic identifies the first series of custom graphics;
   synchronizing the placement of the first set of absorbent articles into the package labeled with the first package identity graphic;
   splicing a third length of the second substrate to the second length of the second substrate;
   subsequently combining the third length of the second substrate with the advancing first substrate in the converting operation;
   and;
   subsequently converting the combined third length of the second substrate and advancing first substrate into disposable absorbent articles.

2. The method of claim 1, further comprising the steps of:
   receiving a second order for disposable absorbent articles having custom graphics;
   printing a second series of custom graphics onto the second length of the second substrate, wherein the second series of custom graphics includes the custom graphics from the second order;
   detecting the second series of custom graphics on the second length of the second substrate;
   converting the combined second length of the second substrate and advancing first substrate into a second set of custom disposable absorbent articles, wherein the second set of custom disposable absorbent articles includes the second series of custom graphics;
   labeling a second package with a second package identity graphic, wherein the second package identity graphic identifies the second series of custom graphics; and
   synchronizing the placement of the second set of disposable absorbent articles into the package labeled with the second set of disposable absorbent articles.

3. The method of claim 1, wherein the step of detecting the first series of custom graphics on the second length of the second substrate includes detecting article identity graphics on the second length of the second substrate that correspond with the first order.

4. The method of claim 1, wherein the first series of custom graphics are article identity graphics.

5. The method of claim 1, wherein the disposable absorbent articles are diapers and wherein the second substrate is a backsheet.

6. The method of claim 1, wherein the first series of custom graphics are printed off line with an inkjet process.

7. The method of claim 6, wherein the second substrate is a film material.

8. The method of claim 7, further comprising the steps of:
   flexographically printing a repeating series of graphics on the first substrate comprising a nonwoven material, wherein each of the graphics of the repeating series are different from each other; and
   combining the film material with the nonwoven material such that the custom graphics on the film material are visible through the nonwoven material.

9. The method of claim 8, wherein the repeating series of graphics on the first substrate include 10 or more graphics different from each other.

10. The method of claim 1, wherein the first product identity graphic is printed directly on the first package.

11. The method of claim 1, wherein the first product identity graphic is printed on a label that is affixed to the first package.

* * * * *